(12) United States Patent
Yamazaki

(10) Patent No.: US 12,383,487 B2
(45) Date of Patent: *Aug. 12, 2025

(54) CLEANING AGENT

(71) Applicant: KAO CORPORATION, Tokyo (JP)

(72) Inventor: Naoyuki Yamazaki, Sumida-ku (JP)

(73) Assignee: KAO CORPORATION, Tokyo (JP)

( * ) Notice: Subject to any disclaimer, the term of this patent is extended or adjusted under 35 U.S.C. 154(b) by 617 days.

This patent is subject to a terminal disclaimer.

(21) Appl. No.: 17/764,084

(22) PCT Filed: Mar. 27, 2020

(86) PCT No.: PCT/JP2020/014344
§ 371 (c)(1),
(2) Date: Mar. 25, 2022

(87) PCT Pub. No.: WO2021/065045
PCT Pub. Date: Apr. 8, 2021

(65) Prior Publication Data
US 2022/0273554 A1 Sep. 1, 2022

(30) Foreign Application Priority Data
Sep. 30, 2019 (JP) .................. 2019-180411

(51) Int. Cl.
| | | |
|---|---|---|
| C11D 1/00 | (2006.01) |
| A61K 8/37 | (2006.01) |
| A61K 8/39 | (2006.01) |
| A61K 8/44 | (2006.01) |
| A61K 8/46 | (2006.01) |
| A61K 8/73 | (2006.01) |
| A61K 8/81 | (2006.01) |
| A61K 8/891 | (2006.01) |
| A61K 8/898 | (2006.01) |
| A61Q 5/02 | (2006.01) |
| C11D 1/66 | (2006.01) |
| C11D 1/88 | (2006.01) |
| C11D 3/37 | (2006.01) |

(52) U.S. Cl.
CPC ............... *A61K 8/898* (2013.01); *A61K 8/39* (2013.01); *A61K 8/442* (2013.01); *A61K 8/447* (2013.01); *A61K 8/463* (2013.01); *A61K 8/731* (2013.01); *A61Q 5/02* (2013.01); *A61K 2800/596* (2013.01)

(58) Field of Classification Search
CPC .... C11D 1/00; C11D 1/66; C11D 1/88; C11D 3/162; C11D 3/3742; C11D 3/3796; A61K 8/37; A61K 8/39; A61K 8/44; A61K 8/46; A61K 8/73; A61K 8/81; A61K 8/891; A61K 8/898; A61Q 5/02
See application file for complete search history.

(56) References Cited

U.S. PATENT DOCUMENTS

| | | | |
|---|---|---|---|
| 2001/0051142 A1 | 12/2001 | Duden et al. | |
| 2009/0041707 A1 | 2/2009 | Molenda et al. | |
| 2011/0150810 A1* | 6/2011 | Molenda ................. | A61Q 5/12 424/70.21 |
| 2015/0047665 A1 | 2/2015 | Lehman et al. | |
| 2019/0117543 A1* | 4/2019 | Zhao ..................... | A61K 31/60 |

FOREIGN PATENT DOCUMENTS

| | | |
|---|---|---|
| CA | 2 341 343 A1 | 9/2001 |
| JP | 2012-232953 A | 11/2012 |
| JP | 2013-517337 A | 5/2013 |
| JP | 2013-540152 A | 10/2013 |
| JP | 2014-528967 A | 10/2014 |

OTHER PUBLICATIONS

Extended European Search Report issued Oct. 27, 2023 in European Patent Application No. 20870503.8, 10 pages.
International Search Report issued on Jun. 16, 2020 in PCT/JP2020/014344 filed on Mar. 27, 2020, 2 pages.

* cited by examiner

*Primary Examiner* — Brian P Mruk
(74) *Attorney, Agent, or Firm* — Oblon, McClelland, Maier & Neustadt, L.L.P.

(57) ABSTRACT

A detergent comprising (A) an anionic surfactant, (B) a quaternary ammonium cation-modified silicone, and (C) a cationic polymer is described. A mass ratio [(A)/(B)] of the component (A) to the component (B) is 30 or more and 5,000 or less, and a mass ratio [(B)/(C)] of the component (B) to the component (C) is 0.01 or more and 0.5 or less.

9 Claims, No Drawings

CLEANING AGENT

FIELD OF THE INVENTION

The present invention relates to a detergent.

BACKGROUND OF THE INVENTION

There is a demand for a hair cosmetic capable of reducing the time and effort in daily hair-care activities and leading a hair-care life without stress. In particular, in the field of hair detergents, in addition to the basic function of removing hair stains, research has been conducted on hair detergents having a good feeling of use, such as good lathering, and putting fingers through hair during washing and after rinsing.

In such hair detergents, ones having a cationized silicone blended therein are known. For example, JP 2013-517337 A (PTL 1) describes that a polysiloxane of a specified structure containing quaternary ammonium groups and being branched in the siloxane moiety, becomes an active ingredient capable of imparting combability, softness, detanglability of damaged and undamaged hair, sheen, and the like and discloses formulations blended in shampoos, hair rinses, conditioners, and so on.

JP 2014-528967 A (PTL 2) discloses that when a microemulsion containing, as oil phase, a polysiloxane of a specified structure containing at least one quaternary ammonium group is used for shampoos and hair rinses, the evaluations regarding wet combability, dry combability, feel, and shine are good.

SUMMARY OF THE INVENTION

The present invention relates to a detergent containing
(A) an anionic surfactant,
(B) a quaternary ammonium cation-modified silicone, and
(C) a cationic polymer,
wherein a mass ratio [(A)/(B)] of the component (A) to the component (B) is 30 or more and 5,000 or less, and a mass ratio [(B)/(C)] of the component (B) to the component (C) is 0.01 or more and 0.5 or less.

DETAILED DESCRIPTION OF THE INVENTION

The hair is damaged by the living environment (ultraviolet rays or heat of sunlight), the daily hair-care activities (friction by hair washing or brushing), and the chemical treatment (coloring, perm, etc.). When the damaged hairs rub against each other, a large frictional force is generated on the surface, and entanglement is caused. The "entanglement of hair" is a cause of all of stresses in the hair-care activities, and there was involved such a problem that when the entanglement of hair is once generated, it is difficult to dissociate the entanglement. Although the entanglement of hair is possibly generated during hair washing, during conditioning, after towel drying, or during drying with a hair dryer or the like, according to the research made by the present inventor, it has been noted that when the entanglement of hair is generated at the stage of hair washing, even if a conditioning treatment is subsequently performed, it is difficult to completely dissociate the entanglement. Accordingly, it is preferred that the entanglement of hair can be inhibited or solved during hair washing.

In particular, when performing an action to allow hairs to rub against each other by, for example, towel drying, the hairs which have been dissociated through the conditioning treatment are again strongly entangled in cooperation with friction with the towel. Accordingly, massive time and effort are taken for the action to dissociate the entanglement in addition to drying, and a long time is required for drying.

PTLs 1 and 2 do not disclose inhibition and solution of the entanglement of hair on the occasion of hair washing, in particular, spontaneous dissociation of the entanglement of hair without performing an operation of putting fingers through hair or the like.

The present invention is concerned with a detergent that is favorable in lathering during washing and is able to inhibit and solve the generation of entanglement of a washing object, such as hair and fibers, even during washing and after washing without performing an operation of putting fingers through hair or the like.

The present inventor has found that the aforementioned problem can be solved by a detergent containing an anionic surfactant, a quaternary ammonium cation-modified silicone, and a cationic polymer in a predetermined proportion.

Specifically, the present invention relates to a detergent containing
(A) an anionic surfactant,
(B) a quaternary ammonium cation-modified silicone, and
(C) a cationic polymer,
wherein a mass ratio [(A)/(B)] of the component (A) to the component (B) is 30 or more and 5,000 or less, and a mass ratio [(B)/(C)] of the component (B) to the component (C) is 0.01 or more and 0.5 or less.

In accordance with the detergent of the present invention, lathering during washing is favorable, and the generation of entanglement of a washing object, such as hair and fibers, even during washing and after washing can be substantially inhibited and solved without performing an operation of putting fingers through hair or the like. For example, in the case where the detergent of the present invention is a hair detergent, the entanglement in hair after washing and towel drying is hardly generated, and therefore, the hair can be dried for a short time, and finish after drying becomes favorable.

[Detergent]

The detergent of the present invention is a detergent containing
(A) an anionic surfactant,
(B) a quaternary ammonium cation-modified silicone, and
(C) a cationic polymer,
wherein a mass ratio [(A)/(B)] of the component (A) to the component (B) is 30 or more and 5,000 or less, and a mass ratio [(B)/(C)] of the component (B) to the component (C) is 0.01 or more and 0.5 or less.

In view of the fact that the detergent of the present invention has the aforementioned constitution, it is favorable in lathering during washing and is able to effectively inhibit and solve the generation of entanglement of a washing object, such as hair and fibers, during washing and even after washing. For example, in the case where the detergent of the present invention is a hair detergent, only by washing the hair with the foregoing hair detergent, the entanglement of hair can be inhibited, and even when an operation of performing an operation of putting fingers through hair or the like is not performed, the entanglement of hair can be spontaneously dissociated. The expression "one containing the components (A), (B), and (C)" also means "one prepared by blending the components (A), (B), and (C)".

Although the reason why in view of the fact that the detergent of the present invention has the aforementioned constitution, the effects of the present invention are brought is not elucidated yet, the following may be conjectured.

In order to reveal such a state that the entanglement of hair or the like is spontaneously dissociated during washing and after washing of hair or fibers, it may be considered to be important to lower a frictional force working on the hair or between the fibers. In a hair detergent, a silicone is generally blended as an active ingredient; however, the present inventor has found that in order that a frictional force working on the hair or between the fibers may be lowered and further the entanglement of hair or the like may be spontaneously dissociated, it is effective to not only use a quaternary ammonium cation-modified silicone having high hydrophilicity (component (B)) but also blend the component (B) in a predetermined proportion relative to an anionic surfactant that is the component (A) in the presence of a cationic polymer that is the component (C) in a fixed concentration. The component (B) has a hydrophilic quaternary ammonium cation moiety, is water-soluble as compared to silicones having high hydrophobicity, is high in hydrophilicity, and is able to readily enter an entangled site with hair or fibers during washing, so that it may be considered that the component (B) acts effectively on hair or fiber to exhibit a high effect for allowing the entanglement of hair or the like to be spontaneously dissociated. Here, the wording "water-soluble" as referred to in this specification means that the solubility in water at 25° C. is 0.1 g/100 g or more.

On the other hand, in order to exhibit a function to remove the entanglement of hair or the like, it is preferred to allow a sufficient amount of the component (B) to remain on the hair or the like. However, since while the component (B) is an oil component, it has solubility in water, its retainability on the hair or the like is weak, and in the case where the component (B) is contained in the detergent containing the component (A) that is the anionic surfactant and used for washing the hair or the like, the detergent is diluted with a large quantity of water, and at the same time, the component (B) is washed away, so that the function to remove the entanglement cannot be sufficiently exhibited. In the detergent of the present invention, by blending the component (C) that is the cationic polymer in a predetermined proportion, the anionic component (A) and the cationic component (C) form coacervation under circumstances such that the detergent is diluted with a large quantity of water, and the component (B) is included within the coacervation, whereby the component (B) can be efficiently adsorbed onto the hair, and thus, it may be considered that the effects of the present invention can be exhibited. In general, though the coacervation refers to a phenomenon in which a concentrated colloid sol is separated from the homogeneous solution, in the present invention, it refers to a phenomenon in which the anionic surfactant and the cationic polymer form a water-insoluble complex to cause phase separation. In addition, by using the component (C), the feel on the hair or the like after washing is improved, too.

When towel drying is performed in a state that the entanglement of hair is dissociated, a contact area between the hair and the towel increases so that the moisture of the hair is quickly absorbed onto the towel. In addition, it may be considered that a contact area between the hair and air increases during drying with a hair dryer or during natural drying, and the moisture in the hair is quickly transpired, so that a drying speed of the hair is improved.

From the viewpoint of effectively obtaining the effects of the present invention, the detergent of the present invention is preferably a hair detergent or a detergent for fibers, and more preferably a hair detergent.

A dosage form of the detergent is not particularly limited, and it is possible to adopt an arbitrary dosage form, for example, a liquid form, a lathering form, a paste form, a cream form, a solid form, or a powder form. For example, in the case of a hair detergent, a liquid form, a paste form or a cream form is preferred, and a liquid form is more preferred.

<Component (A): Anionic Surfactant>

The detergent of the present invention contains the anionic surfactant as the component (A). The component (A) is used for the purpose of imparting detergency.

Examples of the anionic surfactant include alkylbenzenesulfonic acid salts, alkyl or alkenyl ether sulfuric acid salts, alkyl or alkenyl sulfuric acid salts, alkylsulfonic acid salts, saturated or unsaturated fatty acid salts, alkyl or alkenyl ether carboxylic acid salts, α-sulfo fatty acid salts, N-acylamino acids, phosphoric acid mono- or diesters, and sulfosuccinic acid esters. Of these, one or more thereof may be used.

Examples of a counter ion of the anionic group of the anionic surfactant include alkali metal ions, such as a sodium ion and a potassium ion; alkaline earth metal ions, such as a calcium ion and a magnesium ion; an ammonium ion; and alkanol ammoniums having 1 to 3 alkanol groups having 2 or 3 carbon atoms (for example, monoethanolammonium, diethanolammonium, triethanolammonium, and triisopropanolammonium).

Above all, from the viewpoint of lathering during washing, the component (A) is preferably at least one selected from the group consisting of alkyl sulfuric acid salts, alkyl ether sulfuric acid salts, and alkyl ether carboxylic acid salts. Examples of the alkyl ether sulfuric acid salt include polyoxyethylene alkyl ether sulfuric acid salts, such as ammonium laureth sulfate; and examples of the alkyl ether carboxylic acid salts include polyoxyethylene alkyl ether acetic acid salts, such as sodium laureth carboxylate.

From the viewpoint of lathering during washing, the compound (A) is more preferably at least one selected from the group consisting of alkyl ether sulfuric acid salts and alkyl ether carboxylic acid salts; still more preferably at least one selected from the group consisting of polyoxyethylene alkyl ether sulfuric acid salts and polyoxyethylene alkyl ether acetic acid salts; and yet still more preferably at least one selected from the group consisting of polyoxyethylene lauryl ether ammonium sulfate (ammonium laureth sulfate) and polyoxyethylene lauryl ether sodium acetate (sodium laureth carboxylate).

From the viewpoint of lathering during washing and inhibition and solution of entanglement of a washing object, such as hair, and the viewpoint of reduction in entanglement during hair rinsing, easiness of brushing after towel drying, and quick drying properties in the hair detergent, the content of the component (A) in the detergent is preferably 1% by mass or more, more preferably 3% by mass or more, still more preferably 5% by mass or more, and yet still more preferably 7% by mass or more, and from the same viewpoints, it is preferably 30% by mass or less, more preferably 20% by mass or less, and still more preferably 18% by mass or less. A specific range of the content of the component (A) in the detergent is preferably 1 to 30% by mass, more preferably 3 to 20% by mass, still more preferably 5 to 18% by mass, and yet still more preferably 7 to 18% by mass.

<Component (B): Quaternary Ammonium Cation-Modified Silicone>

The detergent of the present invention contains the quaternary ammonium cation-modified silicone as the component (B). In view of the fact that the detergent of the present invention contains the component (B), in the washing object, such as hair and fibers, the generation of entanglement can be effectively inhibited and solved owing to the aforementioned mechanism of action even during washing and after washing.

The quaternary ammonium cation-modified silicone that is used in the present invention may be a silicone containing at least one quaternary ammonium group in a main chain or side chain moiety of a polysiloxane. More specifically, the component (B) is preferably a quaternary ammonium cation-modified silicone having at least one structure selected from the group consisting of a structure represented by the following general formula (1) and a structure represented by the following general formula (2).

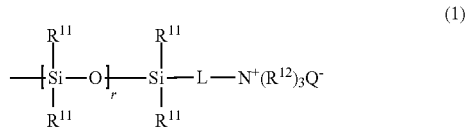

(1)

In the formula (1), $R^{11}$ represents a hydrocarbon group having 1 or more and 6 or less carbon atoms. $R^{12}$ represents a hydrogen atom, a hydrocarbon group having 1 or more and 20 or less carbon atoms, or an amide bond-containing hydrocarbon group having 1 or more and 20 or less carbon atoms. L represents a divalent organic group. $Q^-$ is a counter ion of the quaternary ammonium ion. r represents a number of 2 or more. Plural $R^{11}$'s and $R^{12}$'s may be the same as or different from each other. In addition, the bonding order among the structural units within the bracket does not matter, and the bonding form may be a block form or a random form.

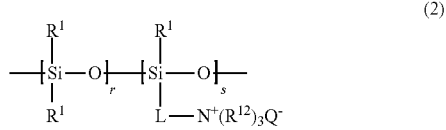

(2)

In the formula (2), $R^{11}$, $R^{12}$, L, $Q^-$, and r are the same as mentioned above. s is a number of 1 or more. Plural $R^{11}$'s and $R^{12}$'s may be the same as or different from each other. In addition, the bonding order among the structural units within the bracket does not matter, and the bonding form may be a block form or a random form.

In the general formulae (1) and (2), $R^{11}$'s are each independently preferably an alkyl group having 1 or more and 6 or less carbon atoms or a phenyl group, more preferably a methyl group or an ethyl group, and still more preferably a methyl group.

In the general formulae (1) and (2), $R^{12}$ is preferably a hydrocarbon group having 1 or more and 20 or less carbon atoms or an amide bond-containing hydrocarbon group having 1 or more and 20 or less carbon atoms, and at least one of plural existent $R^{12}$'s is more preferably an amide bond-containing hydrocarbon group having 1 or more and 20 or less carbon atoms.

In the general formulae (1) and (2), L is preferably $*^1$—$R^{13}$—$CH_2$—$CHOH$—$CH_2$—$*^2$. Here, $R^{13}$ is a divalent organic group, preferably an alkylene group having 1 or more and 20 or less carbon atoms or an oxyalkylene group having 1 or more and 20 or less carbon atoms, more preferably an oxyalkylene group having 1 or more and 20 or less carbon atoms, and still more preferably an oxyalkylene group having 2 or more and 6 or less carbon atoms. $*^1$ represents a binding site to the silicon atom, and $*^2$ represents a binding site to the nitrogen atom.

In the general formulae (1) and (2), r is preferably a number of 2 or more and 200 or less, and more preferably a number of 2 or more and 100 or less.

In the general formula (2), s is preferably a number of 1 or more and 50 or less, more preferably a number of 2 or more and 20 or less, and still more preferably a number of 2 or more and 10 or less.

In the general formulae (1) and (2), $Q^-$ represents an anion, such as a halide ion, e.g., a chloride ion and a bromide ion; and an organic acid ion, e.g., an alkyl sulfate ion having 1 or more and 3 or less carbon atoms, an acetate ion, a lactate ion, a benzoate ion, an adipate ion, a formate ion, a malate ion, a citrate ion, and a glycolate ion. Of these, an organic acid ion is preferred, and an acetate ion or a lactate ion is more preferred.

From the viewpoint of lathering during washing and inhibition and solution of entanglement of a washing object, such as hair, and the viewpoint of reduction in entanglement during hair rinsing, easiness of brushing after towel drying, and quick drying properties in the hair detergent, and the viewpoint of easiness of blending, the component (B) is preferably a quaternary ammonium cation-modified silicone having the structure represented by the general formula (1). The component (B) is more preferably at least one selected from the group consisting of a quaternary ammonium cation-modified silicone represented by the following general formula (1-1) and a quaternary ammonium cation-modified silicone represented by the following general formula (1-2).

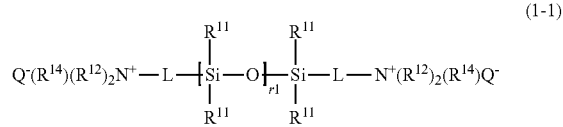

(1-1)

In the formula (1-1), $R^{11}$ represents a hydrocarbon group having 1 or more and 6 or less carbon atoms. $R^{12}$ represents a hydrogen atom, a hydrocarbon group having 1 or more and 20 or less carbon atoms, or an amide bond-containing hydrocarbon group having 1 or more and 20 or less carbon atoms. $R^{14}$ represents a hydrocarbon group having 1 or more and 20 or less carbon atoms or an amide bond-containing hydrocarbon group having 1 or more and 20 or less carbon atoms. L represents a divalent organic group. $Q^-$ is a counter ion of the quaternary ammonium ion. r1 represents a number of 2 or more. Plural $R^{11}$'s and $R^{12}$'s may be the same as or different from each other. In addition, the bonding order among the structural units within the bracket does not matter, and the bonding form may be a block form or a random form.

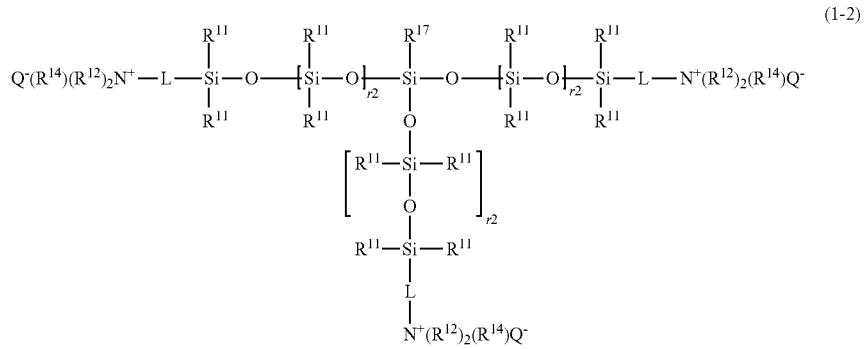

(1-2)

In the formula (1-2), $R^{11}$, $R^{12}$, $R^{14}$, L, and $Q^-$ are the same as mentioned above. $R^{17}$ represents an alkyl group having 1 or more and 6 or less carbon atoms or a phenyl group. r2 represents a number of 2 or more. In addition, the bonding order among the structural units within the bracket does not matter, and the bonding form may be a block form or a random form.

In the general formulae (1-1) and (1-2), $R^{11}$'s are the same as exemplified in the general formula (1) and are each independently preferably an alkyl group having 1 or more and 6 or less carbon atoms or a phenyl group, more preferably a methyl group or an ethyl group, and still more preferably a methyl group.

In the general formulae (1-1) and (1-2), $R^{12}$ is the same as exemplified in the general formula (1) and is preferably a hydrocarbon group having 1 or more and 20 or less carbon atoms, and more preferably a methyl group.

In the general formulae (1-1) and (1-2), L is the same as exemplified in the general formula (1) and is preferably $*^1$—$R^{13}$—$CH_2$—CHOH—$CH_2$—$*^2$. Here, $R^{13}$ is preferably an alkylene group having 1 or more and 20 or less carbon atoms or an oxyalkylene group having 1 or more and 20 or less carbon atoms, more preferably an oxyalkylene group having 1 or more and 20 or less carbon atoms, and still more preferably an oxyalkylene group having 2 or more and 6 or less carbon atoms. $*^1$ represents a binding site to the silicon atom, and $*^2$ represents a binding site to the nitrogen atom.

In the general formulae (1-1) and (1-2), $R^{14}$ is preferably a hydrocarbon group having 1 or more and 20 or less carbon atoms or an amide group-containing hydrocarbon group having 1 or more and 20 or less carbon atoms, more preferably an amide group-containing hydrocarbon group having 1 or more and 20 or less carbon atoms, and sill more preferably —$R^{15}$—NHCO—$R^{16}$.

Here, $R^{15}$ is an alkylene group or an oxyalkylene group each having 1 or more and 18 or less carbon atoms, preferably an alkylene group having 1 or more and 18 or less carbon atoms, and more preferably an alkylene group having 2 or more and 6 or less carbon atoms. $R^{16}$ is an alkyl group having 1 or more and 18 or less carbon atoms, and preferably an alkyl group having 8 or more and 18 or less carbon atoms.

In the general formula (1-2), $R^{17}$ is preferably an alkyl group having 1 or more and 6 or less carbon atoms or a phenyl group, and more preferably a phenyl group.

In the general formula (1-1), r1 is preferably a number of 2 or more and 200 or less, more preferably a number of 2 or more and 100 or less, still more preferably a number of 10 or more and 100 or less, and yet still more preferably a number of 20 or more and 100 or less.

In the general formula (1-2), r2 is preferably a number of 2 or more and 200 or less, and more preferably a number of 2 or more 100 or less.

In the general formulae (1-1) and (1-2), $Q^-$ is the same as exemplified in the general formula (1) and represents an anion, such as a halide ion, e.g., a chloride ion and a bromide ion; or an organic acid ion, e.g., an alkyl sulfate ion having 1 or more and 3 or less carbon atoms, an acetate ion, a lactate ion, a benzoate ion, an adipate ion, a formate ion, a malate ion, a citrate ion, and a glycolate ion. Of these, an organic acid ion is preferred, and an acetate ion or a lactate ion is more preferred.

Among the quaternary ammonium cation-modified silicones represented by the general formula (1-1), a quaternary ammonium cation-modified silicone represented by the following general formula (1-3) is more preferred; and among the quaternary ammonium cation-modified silicones represented by the general formula (1-2), a quaternary ammonium cation-modified silicone represented by the following general formula (1-4) is more preferred.

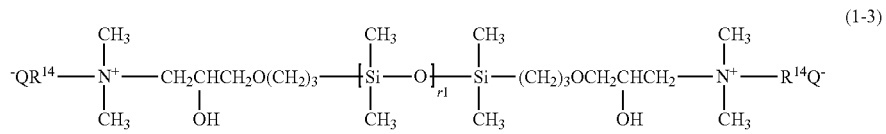

(1-3)

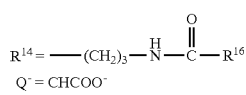

$Q^- = CHCOO^-$

In the general formula (1-3), r1 is the same as mentioned above. $R^{16}$ is an alkyl group having 8 or more and 18 or less carbon atoms.

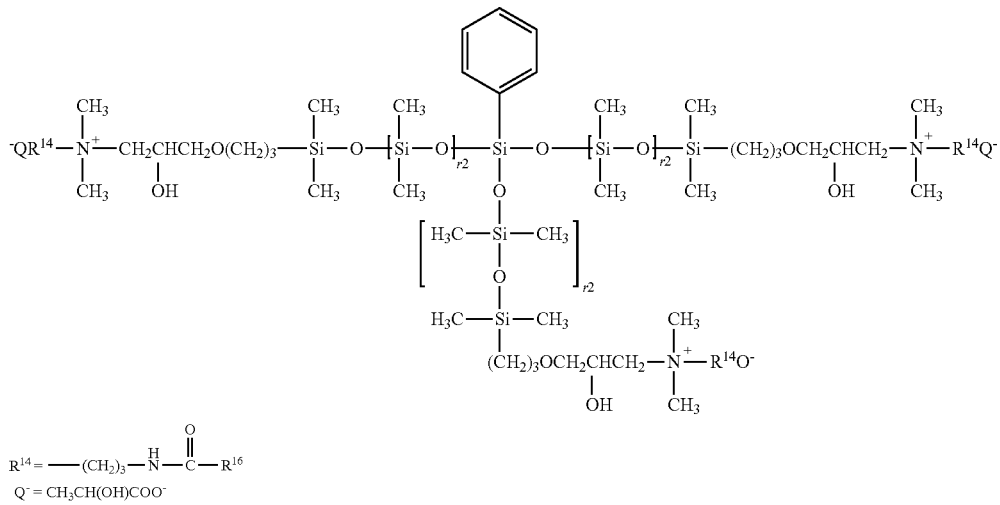

(1-4)

In the general formula (1-4), r2 is the same as mentioned above. $R^{16}$ is an alkyl group having 8 or more and 18 or less carbon atoms.

As the quaternary ammonium cation-modified silicone represented by the general formula (1-3), there is exemplified Quaternium-80. Specific examples thereof include "ABIL QUAT 3272" (r1=30) and "ABIL QUAT 3474" (r1=80), both of which are manufactured by Evonik Industries AG.

As the quaternary ammonium cation-modified silicone represented by the general formula (1-4), there is exemplified Silicone Quaternium-22. Specific examples thereof include "ABIL TQUAT60" and "ABIL ME 45", both of which are manufactured by Evonik Industries AG.

Examples of the quaternary ammonium cation-modified silicone other than Quaternium-80 and Silicone Quaternium-22 include Silicone Quaternium-1, Silicone Quaternium-2, Silicone Quaternium-3, Silicone Quaternium-4, Silicone Quaternium-5, Silicone Quaternium-6, Silicone Quaternium-7, Silicone Quaternium-8, Silicone Quaternium-9, Silicone Quaternium-10, Silicone Quaternium-11, Silicone Quaternium-12, Silicone Quaternium-15, Silicone Quaternium-16, Silicone Quaternium-17, Silicone Quaternium-18, Silicone Quaternium-20, Silicone Quaternium-21, Silicone Quaternium-2 Panthenol Succinate, and Silicone Quaternium-16/Glycidyl Dimethicone Crosspolymer.

The component (B) may be used alone or in combination of two or more thereof.

In the detergent of the present invention, from the viewpoint of lathering during washing and inhibition and solution of entanglement of a washing object, such as hair, and the viewpoint of reduction in entanglement during hair rinsing, easiness of brushing after towel drying, and quick drying properties in the hair detergent, and the viewpoint of easiness of blending, a mass ratio [(A)/(B)] of the component (A) to the component (B) is 30 or more, preferably 35 or more, more preferably 40 or more, still more preferably 45 or more, yet still more preferably 50 or more, even yet still more preferably 55 or more, even still more preferably 60 or more, and even still more further preferably 65 or more; and it is 5,000 or less, preferably 3,000 or less, more preferably 2,000 or less, still more preferably 1,500 or less, yet still more preferably 1,200 or less, even yet still more preferably 1,000 or less, even still more preferably 700 or less, even still more further preferably 500 or less, even yet still more further preferably 300 or less, and more even yet still more further preferably 200 or less. A specific range of the mass ratio [(A)/(B)] of the component (A) to the component (B) in the detergent is 30 to 5,000, preferably 35 to 3,000, more preferably 40 to 2,000, still more preferably 40 to 1,500, yet still more preferably 45 to 1,200, even yet still more preferably 50 to 1,200, even still more preferably 50 to 1,000, even still more further preferably 50 to 700, even yet still more further preferably 50 to 500, more even yet still more further preferably 50 to 300, yet more yet still more further preferably 55 to 300, yet more yet still more further preferably 60 to 300, yet more yet still more further preferably 65 to 300, and yet more yet still more further preferably 65 to 200.

Although the content of the component (B) in the detergent may be the amount at which the mass ratio [(A)/(B)] is 30 or more and 5,000 or less, from the viewpoint of inhibition and solution of entanglement of a washing object, such as hair, and the viewpoint of reduction in entanglement during hair rinsing, easiness of brushing after towel drying, and quick drying properties in the hair detergent, it is preferably 0.001% by mass or more, more preferably 0.005% by mass or more, and still more preferably 0.01% by mass or more, and from the viewpoint of lathering during washing, it is preferably 3% by mass or less, more preferably 1% by mass or less, still more preferably 0.7% by mass or less, yet still more preferably 0.5% by mass or less, even yet still more preferably 0.3% by mass or less, and even still more preferably 0.2% by mass or less. A specific range of the content of the component (B) in the detergent is preferably 0.001 to 3% by mass, more preferably 0.005 to 1% by mass, still more preferably 0.005 to 0.7% by mass, yet still more preferably 0.01 to 0.5% by mass, even yet still more preferably 0.01 to 0.3% by mass, and even still more preferably 0.01 to 0.2% by mass.

<Component (C): Cationic Polymer>

For the purpose of lathering during washing and strengthening reduction in entanglement during hair rinsing, easiness of brushing after towel drying, and quick drying properties in the hair detergent, the detergent of the present invention further contains, as a component (C), a cationic polymer. In this specification, the "cationic polymer" refers to a water-soluble polymer having a cationic group and having a cationic charge as a whole, and the cationic group refers to a cation group or a group capable of being ionized to become a cation group. Specifically, examples thereof include a primary amino group, a secondary amino group, a tertiary amino group, and a quaternary ammonium group. The component (C) is a cationic polymer other than the component (B) and a component (B') as mentioned later.

Examples of the cationic polymer that is used as the component (C) include a cationized polygalactomannan, such as cationized guar gum, cationized tara gum, and cationized locust bean gum; a cationized cellulose; a cationized hydroxyalkyl cellulose, such as cationized hydroxyethyl cellulose and cationized hydroxypropyl cellulose; a cationic starch; a cationized polyvinyl alcohol; a quaternized dialkylaminoalkyl (meth)acrylic acid salt polymer, such as a vinylpyrrolidone/N,N-dimethylaminoethyl methacrylic acid diethyl sulfate copolymer and an N,N-dimethylaminoethyl methacrylic acid diethyl sulfate/N,N-dimethylacrylamide/dimethacrylic acid polyethylene glycol copolymer; a diallyl quaternary ammonium salt polymer, such as a polydiallylklimethylammonium chloride, a diallyldimethylammonium chloride/acrylic acid copolymer, a diallyldimethylammonium chloride/acrylamide copolymer, and a diallyldimethylammonium chloride/acrylic acid/acrylamide copolymer; a vinylimidazolium trichloride/vinylpyrrolidone copolymer; a vinylpyrrolidone/alkylaminoalkyl (meth)acrylate copolymer; a vinylpyrrolidone/alkylaminoalkyl (meth)acrylate/vinyl caprolactam copolymer; a vinylpyrrolidone/(meth)acrylamide propyl trimethylammonium chloride copolymer; an alkyl acrylamide/(meth)acrylate/alkylaminoalkyl acrylamide/polyethylene glycol (meth)acrylate copolymer; an adipic acid/dimethylaminohydroxypropyl ethylene triamine copolymer; and cationic polymers described in JP 53-139734 A and JP 60-36407 A. These may be used alone or in combination of two or more thereof. Of these, at least one selected from the group consisting of a cationized polygalactomannan, a cationized hydroxyalkyl cellulose, a quaternized dialkylaminoalkyl (meth)acrylic acid salt polymer, and a diallyl quaternary ammonium salt polymer is preferred; and at least one selected from the group consisting of cationized guar gum, a cationized hydroxyalkyl cellulose, and a quaternized dialkylaminoalkyl (meth)acrylic acid salt polymer is more preferred.

As a commercially available cationic polymer that may be used as the component (C), for example, the following may be exemplified.

(Cationized Guar Gum)
    JAGUAR Excel, JAGUAR C-17, and JAGUAR C-14-S (all of which are manufactured by Solvay (Novecare)), etc.
(Cationized Terra Gum)
    CATINAL CTR-100 (manufactured by Toho Chemical Industry Co., Ltd.), etc.
(Cationized Locust Bean Gum)
    CATINAL CLB-100 (manufactured by Toho Chemical Industry Co., Ltd.), etc.
(Cationized Hydroxyethyl Cellulose)
    Polyquaternium-10 (o[2-hydroxy-3-(trimethylammonio)propyl]hydroxyethyl cellulose chloride): for example, UCARE POLYMER JR-30M and UCARE POLYMER JR-400 (all of which are manufactured by The Dow Chemical Company), POIZ C-60H and POIZ C-150L (all of which are manufactured by Kao Corporation), etc.
    Polyquaternium-67: SoftCAT (manufactured by The Dow Chemical Company), etc.
(Cationized Hydroxypropyl Cellulose)
    SOFCARE C-HP2W (manufactured by Kao Corporation), etc.
(Cationized Polyvinyl Alcohol)
    GOHSENX K-434 (manufactured by The Nippon Synthetic Chemical Industry Co., Ltd.), CM318 (manufactured by Kuraray Co., Ltd.), etc.
(Vinylpyrrolidone/N,N-Dimethylaminoethyl Methacrylic Acid Diethyl Sulfate Copolymer)
    Polyquaternium-11: GAFQUAT 734 and GAFQUAT 755N (all of which are manufactured by ISP Japan Ltd.), etc.
(N,N-Dimethylaminoethyl Methacrylic Acid Diethyl Sulfate/N,N-Dimethylacrylamide/Dimethacrylic Acid Polyethylene Glycol Copolymer)
    Polyquaternium-52: SOFCARE KG-101E and SOFCARE KG-101W-E (all of which are manufactured by Kao Corporation), etc.
(Polydiallyldimethylammonium Chloride)
    Polyquaternium-6: MERQUAT 100 (manufactured by The Lubrizol Corporation), etc.
(Diallyldimethylammonium Chloride/Acrylic Acid Copolymer)
    Polyquaternium-22: MERQUAT 280 and MERQUAT 295 (all of which are manufactured by The Lubrizol Corporation), etc.
(Diallyldimethylammonium Chloride/Acrylamide Copolymer)
    Polyquaternium-7: MERQUAT 550 (manufactured by The Lubrizol Corporation), etc.
(Diallyldimethylammonium Chloride/Acrylic Acid/Acrylamide Polymer)
    Polyquaternium-39: MERQUAT 3331PR (manufactured by The Lubrizol Corporation), etc.

From the viewpoint of lathering during washing and reduction in entanglement during hair rinsing, easiness of brushing after towel drying, and quick drying properties in the hair detergent, and easiness of blending, a mass ratio [(B)/(C)] of the component (B) to the component (C) in the detergent is 0.01 or more, preferably 0.02 or more, more preferably 0.03 or more, and still more preferably 0.04 or more; and it is 0.5 or less, preferably 0.45 or less, more preferably 0.4 or less, and still more preferably 0.35 or less.

A specific range of the mass ratio [(B)/(C)] of the component (B) to the component (C) in the detergent is 0.01 or more and 0.5 or less, preferably 0.02 to 0.5, more preferably 0.03 to 0.5, still more preferably 0.03 to 0.45, yet still more preferably 0.03 to 0.4, even yet still more preferably 0.04 to 0.4, and even still more preferably 0.04 to 0.35.

Although the content of the component (C) in the detergent may be the amount at which the mass ratio [(B)/(C)] of the component (B) to the component (C) is 0.01 or more and 0.5 or less, from the viewpoint of lathering during washing and reduction in entanglement during hair rinsing, easiness of brushing after towel drying, and quick drying properties in the hair detergent, it is preferably 0.01% by mass or more, more preferably 0.05% by mass or more, still more preferably 0.1% by mass or more, yet still more preferably 0.2% by mass or more, and even yet still more preferably 0.3% by mass or more, and from the viewpoint of lathering during washing and reduction in entanglement during hair rinsing, easiness of brushing after towel drying, and quick drying properties in the hair detergent, and easiness of blending, it is preferably 5% by mass or less, more preferably 3% by mass or less, still more preferably 2% by mass or less, and yet still more preferably 1% by mass or less.

A specific range of the content of the component (C) in the detergent is preferably 0.01 to 5% by mass, more preferably 0.05 to 3% by mass, still more preferably 0.1 to 2% by mass, yet still more preferably 0.2 to 1% by mass, and even yet still more preferably 0.3 to 1% by mass.

From the viewpoint of lathering during washing and reduction in entanglement during hair rinsing, easiness of brushing after towel drying, and quick drying properties in the hair detergent, and easiness of blending, a mass ration [(A)/(C)] of the component (A) to the component (C) in the detergent is preferably 0.1 or more, more preferably 0.5 or more, still more preferably 1 or more, yet still more preferably 3 or more, even yet still more preferably 5 or more, even still more preferably 10 or more, and even still more further preferably 15 or more, and it is preferably 100 or less, more preferably 75 or less, still more preferably 50 or less, yet still more preferably 45 or less, even yet still more preferably 40 or less, and even still more preferably 35 or less.

A specific range of the mass ratio [(A)/(C)] of the component (A) to the component (C) in the detergent is preferably 0.1 to 100, more preferably 0.5 to 75, still more preferably 1 to 50, yet still more preferably 3 to 45, even yet still more preferably 3 to 40, even still more preferably 5 to 40, even still more further preferably 10 to 40, even yet still more further preferably 10 to 35, and more even yet still more further preferably 15 to 35.

<Component (D); Ampholytic Surfactant>

For the purpose of lathering during washing and strengthening reduction in entanglement during hair rinsing, easiness of brushing after towel drying, and quick drying properties in the hair detergent, the detergent of the present invention may further contain, as a component (D), an ampholytic surfactant.

Examples of the ampholytic surfactant include betaine type ampholytic surfactants, amine oxide type ampholytic surfactants, and amino acid type ampholytic surfactants. These may be used alone or in combination of two or more thereof. Of these, betaine type ampholytic surfactants are preferred from the viewpoint of lathering during washing and strengthening reduction in entanglement during hair rinsing, easiness of brushing after towel drying, and quick drying properties in the hair detergent.

Examples of the betaine type ampholytic surfactant include carbobetaine types, such as an alkyl betaine and a fatty acid amidoalkyl betaine, e.g., a fatty acid amidopropyl betaine; sulfobetaine types, such as an alkyl sulfobetaine and an alkylhydroxysulfobetaine; imidazoline-based betaine types; and phosphobetaine types.

As the alkyl betaine, there is exemplified one having an alkyl group having preferably 8 or more and 22 or less carbon atoms, and more preferably 8 or more and 18 or less carbon atoms. Specific examples thereof include lauryldimethylaminoacetic acid betaine and stearyldimethylaminoacetic acid betaine.

As the fatty acid amidoalkyl betaine, there is preferably exemplified a fatty acid amidopropyl betaine. As the fatty acid amidopropyl betaine, there is exemplified one having an acyl group having preferably 8 or more and 22 or less carbon atoms, and more preferably 10 or more and 18 or less carbon atoms. Specific examples thereof include lauric acid amidopropyl betaine [lauramidopropyl betaine], palm kernel oil fatty acid amidopropyl betaine, and coconut oil fatty acid amidopropyl betaine [cocamidopropyl betaine]. Of these, lauric acid amidopropyl betaine [lauramidopropyl betaine] is preferred.

As the alkylsulfobetaine, there is exemplified an alkylsulfobetaine having an alkyl group having preferably 8 or more and 22 or less carbon atoms, and more preferably 8 or more and 18 or less carbon atoms. Specific examples of the alkylsulfobetaine include lauryldimethylsulfoethyl betaine, lauryldimethylsulfopropyl betaine, myristyldimethylsulfoethyl betaine, myristyldimethylsulfopropyl betaine, stearyldimethylsulfoethyl betaine, stearyldimethylsulfopropyl betaine, and coconut oil fatty acid dimethylsulfopropyl betaine.

As the alkylhydroxysulfobetaine, there is exemplified an alkylhydroxysulfobetaine having an alkyl group having preferably 8 or more and 22 or less carbon atoms, and more preferably 8 or more and 18 or less carbon atoms and having at least one hydroxy group. Specific examples of the alkylhydroxysulfobetaine include lauryldimethylsulfo(hydroxyethyl) betaine, lauryldimethylsulfo(hydroxypropyl) betaine [laurylhydroxysultaine], myristyldimethylsulfo(hydroxyethyl) betaine, myristyldimethylsulfo(hydroxypropyl) betaine, stearyldimethylsulfo(hydroxypropyl) betaine, bis-(2-hydroxy-ethyl)sulfoethyl betaine, and lauryl bis-(2-hydroxy-ethyl)sulfopropyl betaine. Of these, lauryldimethylsulfo(hydroxypropyl) betaine [laurylhydroxysultaine] is preferred.

As the imidazoline-based betaine type ampholytic surfactant, there is exemplified an N-acylaminoethyl-N-2-hydroxyethylaminocarboxylic acid salt. Examples thereof include N-coconut oil fatty acid acyl-N'-carboxymethyl-N'-hydroxyethylethylenediamine [also referred to as sodium cocoamphoacetate or 2-alkyl-N-carboxymethyl-N-hydroxyethylimidazolinium betaine], N-coconut oil fatty acid acyl-N'-carboxyethyl-N'-hydroxyethylethylenediamine [sodium cocoamphopropionate], and sodium N-lauroyl-N'-carboxymethyl-N'-hydroxyethylethylenediamine [sodium lauroamphoacetate].

As the phosphobetaine type ampholytic surfactant, there is exemplified lauryl hydroxyphosphobetaine.

The component (D) may be used alone or in combination of two or more thereof.

Among those mentioned above, from the viewpoint of lathering during washing and strengthening reduction in entanglement during hair rinsing, easiness of brushing after towel drying, and quick drying properties in the hair detergent, as the component (D), at least one selected from the group consisting of a carbobetaine type ampholytic surfactant and a sulfobetaine type ampholytic surfactant is preferred, a combination of a carbobetaine type ampholytic surfactant and a sulfobetaine type ampholytic surfactant is more preferred, a combination of a fatty acid amidoalkyl betaine and an alkylhydroxysulfobetaine is still more preferred, and a combination of a fatty acid amidopropyl betaine and an alkylhydroxysulfobetaine is yet still more preferred, and a combination of lauric acid amidopropyl betaine and laurylhydroxysultaine is even yet still more preferred.

In the case of using the component (D), from the viewpoint of lathering during washing and reduction in entanglement during hair rinsing and easiness of brushing after towel drying in the hair detergent, the content of the component (D) in the detergent is preferably 0.01% by mass or more, more preferably 0.1% by mass or more, still more preferably 0.3% by mass or more, and yet still more preferably 0.5% by mass or more, and from the viewpoint of lathering during washing and reduction in entanglement during hair rinsing and easiness of brushing after towel drying in the hair detergent, and easiness of blending, it is preferably 10% by mass or less, more preferably 7% by mass or less, still more preferably 5% by mass or less, and yet still more preferably 3% by mass or less.

A specific range of the content of the component (D) in the detergent is preferably 0.01 to 10% by mass, more preferably 0.1 to 7% by mass, still more preferably 0.3 to 5% by mass, and yet still more preferably 0.5 to 3% by mass.

In the case of using the component (D), from the viewpoint of lathering during washing and reduction in entanglement during hair rinsing, easiness of brushing after towel drying, and quick drying properties in the hair detergent, and easiness of blending, a mass ratio [(A)/(D)] of the component (A) to the component (D) in the detergent is preferably 0.1 or more, more preferably 0.5 or more, still more preferably 1 or more, and yet still more preferably 5 or more, and it is preferably 100 or less, more preferably 75 or less, still more preferably 50 or less, yet still more preferably 30 or less, and even yet still more preferably 20 or less.

A specific range of the mass ratio [(A)/(D)] of the component (A) to the component (D) in the detergent is preferably 0.1 to 100, more preferably 0.5 to 75, still more preferably 1 to 50, yet still more preferably 5 to 30, and even yet still more preferably 5 to 20.

<Component (E): Nonionic Surfactant>

For the purpose of lathering during washing and strengthening reduction in entanglement during hair rinsing in the hair detergent, the detergent of the present invention may be one further contains, as a component (E), a nonionic surfactant.

Examples of the nonionic surfactant include a polyoxyalkylene alkyl ether, a polyoxyalkylene alkenyl ether, a polyoxyalkylene sorbitan fatty acid ester, a polyoxyalkylene fatty acid ester, an alkyl glucoside, an alkyl glyceryl ether, a higher fatty acid sugar ester, a polyglycerin fatty acid ester, a polyoxyethylene hydrogenated castor oil, an alkyl saccharide, an alkylamine oxide, and an alkylamidoamine oxide.

Of these, at least one selected from the group consisting of a polyoxyalkylene alkyl ether, a polyoxyalkylene alkenyl ether, a polyoxyalkylene sorbitan fatty acid ester, a polyoxyalkylene fatty acid ester, an alkyl glucoside, and an alkyl glyceryl ether is preferred; at least one selected from the group consisting of a polyoxyethylene alkyl ether, a polyoxypropylene alkyl ether, an alkyl glucoside, and an alkyl glyceryl ether is more preferred; and at least one selected from a polyoxypropylene alkyl ether, an alkyl glucoside, and an alkyl glyceryl ether is still more preferred.

The carbon number of each of the alkyl group in the polyoxyalkylene alkyl ether, the alkyl glycoside, the alkyl glyceryl ether, the alkyl saccharide, the alkylamine oxide, and the alkylamidoamine oxide; the alkenyl group in the polyoxyalkylene alkenyl ether; and the fatty acid in the polyoxyalkylene sorbitan fatty acid ester, the polyoxyalkylene fatty acid ester, the higher fatty acid sugar ester, and the polyglycerin fatty acid ester is preferably 8 or more and 22 or less, more preferably 8 or more and 18 or less, and still more preferably 8 or more and 12 or less.

As the polyoxyalkylene alkyl ether, there is exemplified a polyoxyethylene alkyl ether or a polyoxypropylene alkyl ether having an alkyl group having preferably 8 or more and 22 or less carbon atoms, more preferably 8 or more and 18 or less carbon atoms, and still more preferably 8 or more and 12 or less carbon atoms. Specific examples thereof include "EMULGEN 103" (Laureth-3: PEG-3 lauryl ether), "EMULGEN 116" (Laureth-16: PEG-16 lauryl ether), and "KAO SOFCARE GP-1" (PPG-3 caprylyl ether), all of which are manufactured by Kao Corporation.

As the alkyl glucoside, there is exemplified an alkyl glucoside having an alkyl group having preferably 8 or more and 22 or less carbon atoms, more preferably 8 or more and 18 or less carbon atoms, and still more preferably 8 or more and 12 or less carbon atoms. Specific examples thereof include "MYDOL 10" (decyl glucoside), manufactured by Kao Corporation; and "Plantaren 2000 N UP" (decyl glucoside) and "Plantacare 818 UP" (coco glucoside), all of which are manufactured by BASF SE.

As the alkyl glyceryl ether, there is exemplified an alkyl glyceryl ether having an alkyl group having preferably 8 or more and 22 or less carbon atoms, more preferably 8 or more and 18 or less carbon atoms, and still more preferably 8 or more and 12 or less carbon atoms. Specific examples thereof include "PENETOL GE-ID" (isodecyl glyceryl ether), manufactured by Kao Corporation. These may be used alone or in combination of two or more thereof.

In the case of using the component (E), from the viewpoint of lathering during washing and strengthening reduction in entanglement during hair rinsing in the hair detergent, the content of the component (E) in the detergent is preferably 0.01% by mass or more, more preferably 0.05% by mass or more, still more preferably 0.1% by mass or more, and yet still more preferably 0.3% by mass or more, and from the viewpoint of lathering during washing and easiness of blending, it is preferably 10% by mass or less, more preferably 5% by mass or less, still more preferably 3% by mass or less, and yet still more preferably 2% by mass or less.

A specific range of the content of the component (E) in the detergent is preferably 0.01 to 10% by mass, more preferably 0.05 to 5% by mass, still more preferably 0.1 to 3% by mass, and yet still more preferably 0.3 to 2% by mass.

In the case of using the component (E), from the viewpoint of lathering during washing and reduction in entanglement during hair rinsing, easiness of brushing after towel drying, and quick drying properties in the hair detergent, and easiness of blending, a mass ratio [(A)/(E)] of the component (A) to the compound (E) in the detergent is preferably 0.1 or more, more preferably 0.5 or more, still more preferably 1 or more, and yet still more preferably 5 or more, and it is preferably 100 or less, more preferably 75 or less, still more preferably 50 or less, and yet still more preferably 30 or less.

A specific range of the mass ratio [(A)/(E)] of the component (A) to the compound (E) in the detergent is preferably 0.1 to 100, more preferably 0.5 to 75, still more preferably 1 to 50, and yet still more preferably 5 to 30.

<Component (B'): Silicone Other Than Component (B)>

From the viewpoint of reduction in entanglement during hair rinsing in the hair detergent, the detergent of the present invention may be one further containing, as a component (B'), a silicone other than the component (B).

Examples of the component (B') include at least one selected from the group consisting of an amino-modified silicone, a polyether-modified silicone, an amino polyether-modified silicone, a dimethylpolysiloxane (dimethicone), a methylphenylpolysiloxane, a fatty acid-modified silicone, an alkoxy-modified silicone, and an alkyl-modified silicone. Of these, at least one selected from the group consisting of an amino-modified silicone, an aminopolyether-modified silicone, and a dimethylpolysiloxane is more preferred, and a dimethylpolysiloxane is still more preferred.

The amino-modified silicone may be any form of an oil, an emulsion, a solution prepared by diluting with a low-viscosity silicone or a liquid paraffin, and so on. The amino-modified silicone is preferably an aminoethylaminopropylsiloxane-dimethylsiloxane copolymer (amodimethicone). Examples of a commercially available product of the amodimethicone include "DOWSIL SM8904" and "DOWSIL CB-1002" (all of which are manufactured by Dow Toray Co., Ltd.); and "KT-0032" and "XF42-B8922" (all of which are manufactured by Momentive Performance Materials Inc.).

The amino polyether-modified silicone is a modified silicone having an amino group and a polyether structure in a main chain or side chain moiety of a polysiloxane, and from the viewpoint of strengthening reduction in entanglement during hair rinsing in the hair detergent, one having a polyoxyalkylene structure is preferred. The carbon number of the alkylene in the polyoxyalkylene structure is preferably 1 or more and 6 or less, and more preferably 2 or more and 4 or less; and at least one selected from the group consisting of ethylene, propylene, trimethylene, and tetramethylene is preferred, and at least one selected from the group consisting of ethylene and propylene is more preferred.

Although the amino polyether-modified silicone may be any form of an oil, an emulsion, and so on, it is preferably an oil. Examples of a commercially available product of the amino polyether-modified silicone include "DOWSIL SILSTYLE 104" ((bisisobutyl PEG-14/amodimethicone) copolymer), "DOWSIL SILSTYLE 201" ((bisisobutyl PEG-14/amodimethicone) copolymer), and "DOWSIL SILSTYLE 401" ((bisisobutyl PEG/PPG-20/35/amodimethicone) copolymer), all of which are manufactured by Dow Toray Co., Ltd.; and "ABIL SOFT AF100" (methoxy PEG/PPG-7/3 aminopropyldimethicone), manufactured by Evonik Industries AG.

The dimethylpolysiloxane may be any form of an oil, an emulsion, a solution prepared by diluting a highly polymerized dimethylpolysiloxane with a low-viscosity silicone or a liquid paraffin, and so on.

Examples of a commercially available product of the dimethylpolysiloxane include SH200 Series (such as SH200C Fluid 1CS, SH200C Fluid 2CS, SH200C Fluid 5CS, SH200C Fluid 10CS, SH200C Fluid 20CS, SH200C Fluid 30CS, SH200C Fluid 50CS, SH200C Fluid 100CS, SH200C Fluid 200CS, SH200C Fluid 350CS, SH200C Fluid 500CS, SH200C Fluid 1,000CS, SH200C Fluid 5,000CS, SH200 Fluid 1.5CS, SH200 Fluid 3,000CS, SH200 Fluid 10,000CS, SH200 Fluid 12,500CS, SH200 Fluid 30,000CS, SH200 Fluid 60,000CS, SH200 Fluid 100,000CS, and SH200 Fluid 1,000,000CS), "DOWSIL BY11-026", "DOWSIL BY22-020", "DOWSIL BY22-029", "DOWSIL BY22-050A", and "DOWSIL BY22-060" (all of which are manufactured by Dow Toray Co., Ltd.); TSF-451 Series (manufactured by Momentive Performance Materials Inc.); and KF-96 Series, KF9008, and KM904 (all of which are manufactured by Shin-Etsu Chemical Co., Ltd.).

In the case of using the component (B'), from the viewpoint of reduction in entanglement during hair rinsing, easiness of brushing after towel drying, and quick drying properties in the hair detergent, the content of the component (B') in the detergent is preferably 0.01% by mass or more, more preferably 0.03% by mass or more, still more preferably 0.05% by mass or more, and yet still more preferably 0.1% by mass or more, and from the viewpoint of lathering during washing and reduction in entanglement during hair rinsing, easiness of brushing after towel drying, and quick drying properties in the hair detergent, and easiness of blending, it is preferably 3% by mass or less, more preferably 2% by mass or less, still more preferably 1.5% by mass or less, and yet still more preferably 1.2% by mass or less.

A specific range of the content of the component (B') in the detergent is preferably 0.01 to 3% by mass, more preferably 0.03 to 2% by mass, still more preferably 0.05 to 1.5% by mass, yet still more preferably 0.1 to 1.5% by mass, and even yet still more preferably 0.1 to 1.2% by mass.

In the case of using the component (B') in the detergent of the present invention, from the viewpoint of lathering during washing and reduction in entanglement during hair rinsing, easiness of brushing after towel drying, and quick drying properties in the hair detergent, and easiness of blending, a mass ratio [(A)/(B')] of the component (A) to the component (B') is preferably 1 or more, more preferably 3 or more, still more preferably 5 or more, and yet still more preferably 10 or more, and it is preferably 500 or less, more preferably 200 or less, still more preferably 100 or less, yet still more preferably 70 or less, even yet still more preferably 50 or less, and even still more preferably 30 or less.

A specific range of the mass ratio [(A)/(B')] of the component (A) to the component (B') is preferably 1 to 500, more preferably 3 to 200, still more preferably 5 to 200, yet still more preferably 10 to 100, even yet still more preferably 10 to 70, even still more preferably 10 to 50, and even still more further preferably 10 to 30.

<Aqueous Medium>

The detergent of the present invention typically contains an aqueous medium. Examples of the aqueous medium include water; lower alcohols, such as ethanol and isopropyl alcohol; and low-molecular diols and triols having 6 or less carbon atoms, such as 1,3-butylene glycol, glycerin, ethylene glycol, and propylene glycol, with water being preferred. Although the content or blending amount of the aqueous medium in the detergent may be appropriately selected according to the dosage form of the detergent, it is typically in a range of 5 to 99% by mass, and preferably in a range of 30 to 98% by mass.

<Other Component>

In the detergent of the present invention, other component may be appropriately contained or blended within a range where the object of the present invention is not impaired. Examples of the other component include materials that are typically blended in a hair detergent, such as an antioxidant, an oil agent, an anti-dandruff agent, a vitamin agent, a disinfectant, an anti-inflammatory agent, an antiseptic, a chelating agent, a moisturizer, a pearlescent agent, a ceramide, a fragrance, and a UV absorber.

<pH>

From the viewpoint of lathering during washing, a pH of the detergent of the present invention is preferably 3.0 or higher, more preferably 3.2 or higher, and still more preferably 4.3 or higher in terms of a pH of a 5% aqueous dispersion, and from the viewpoint of inhibition of entanglement of hair or the like, it is preferably 7.0 or lower, more preferably 6.5 or lower, still more preferably 6.0 or lower, and yet still more preferably 5.6 or lower in terms of a pH of a 5% aqueous dispersion. A specific range of the pH of the 5% aqueous dispersion of the detergent of the present invention is preferably 3.0 to 7.0, more preferably 3.2 to 6.5, still more preferably 4.3 to 6.0, and yet still more preferably 4.3 to 5.6.

The aforementioned pH is a measured value at 25° C., and specifically, it may be measured by the method described in the section of Examples.

A production method of the detergent of the present invention is not particularly limited. For example, the detergent of the present invention may be produced by blending the components (A) to (C) and other components to be used, if desired by the method described in the section of Examples and mixing the contents by using a known agitation apparatus or the like.

A use method of the detergent of the present invention is not particularly limited. The entanglement of hair or fibers during washing and after washing can be prevented through a step of washing a washing object, such as hair and fibers, by a known method by using the detergent of the present invention.

Regarding the aforementioned embodiments, the present invention discloses a detergent and a method of preventing entanglement of hair or fibers.

<1>
A detergent containing:
(A) at least one anionic surfactant selected from the group consisting of an alkyl sulfuric acid salt, an alkyl ether sulfuric acid salt, and an alkyl ether carboxylic acid salt, (B) at least one selected from the group consisting of a quaternary ammonium cation-modified silicone represented by the following general formula (1-1) and a quaternary ammonium cation-modified silicone represented by the following general formula (1-2):

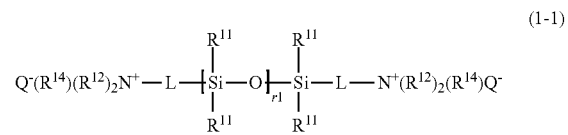

(in the formula (1-1), $R^{11}$ represents a hydrocarbon group having 1 or more and 6 or less carbon atoms; $R^{12}$ represents a hydrogen atom, a hydrocarbon group having 1 or more and 20 or less carbon atoms, or an amide bond-containing hydrocarbon group having 1 or more and 20 or less carbon atoms; $R^{14}$ represents a hydrocarbon group having 1 or more and 20 or less carbon atoms or an amide bond-containing hydrocarbon group having 1 or more and 20 or less carbon atoms; L represents a divalent organic group; $Q^-$ is a counter ion of the quaternary ammonium ion; r1 represents a number of 2 or more; plural $R^{11}$'s and $R^{12}$'s may be the same as or different from each other; and the bonding order among the structural units within the bracket does not matter, and the bonding form may be a block form or a random form), and

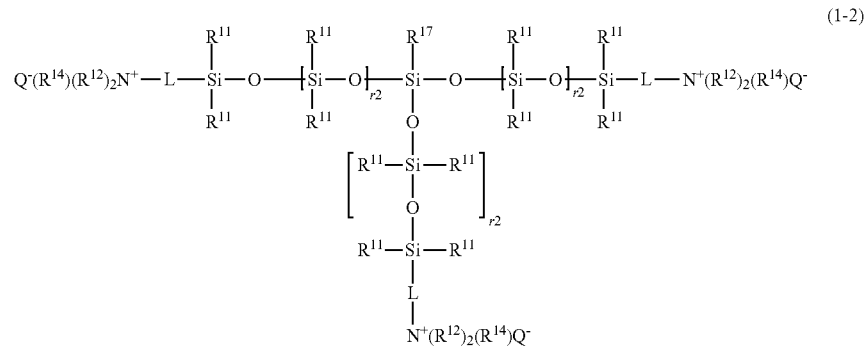

(in the formula (1-2), $R^{11}$, $R^{12}$, $R^{14}$, L, and Q are the same as mentioned above; $R^{17}$ represents an alkyl group having 1 or more and 6 or less carbon atoms or a phenyl group; and r2 represents a number of 2 or more; and the bonding order among the structural units within the bracket does not matter, and the bonding form may be a block form or a random form), and (C) at least one cationic polymer selected from the group consisting of cationized guar gum, a cationized hydroxyalkyl cellulose, and a quaternized dialkylaminoalkyl (meth)acrylic acid salt polymer, wherein,
    a mass ratio [(A)/(B)] of the component (A) to the component (B) is 50 to 1,000, and
    a mass ratio [(B)/(C)] of the component (B) to the component (C) is 0.03 to 0.4.

<2>

The detergent as set forth in <1>, wherein a mass ratio [(A)/(C)] of the component (A) to the component (C) is 10 to 40.

<3>

The detergent as set forth in <1> or <2>, wherein the content of the component (A) in the detergent is 5 to 18% by mass.

<4>

The detergent as set forth in any one of <1> to <3>, wherein the content of the component (B) in the detergent is 0.01 to 0.2% by mass.

<5>

The detergent as set forth in any one of <1> to <4>, wherein the content of the component (C) in the detergent is 0.3 to 1% by mass.

<6>

A detergent containing:

(A) at least one anionic surfactant selected from the group consisting of an alkyl sulfuric acid salt, an alkyl ether sulfuric acid salt, and an alkyl ether carboxylic acid salt, (B) at least one selected from the group consisting of a quaternary ammonium cation-modified silicone represented by the following general formula (1-1) and a quaternary ammonium cation-modified silicone represented by the following general formula (1-2);

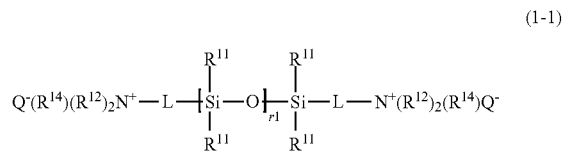

(1-1)

(in the formula (1-1), $R^{11}$ represents a hydrocarbon group having 1 or more and 6 or less carbon atoms; $R^{12}$ represents a hydrogen atom, a hydrocarbon group having 1 or more and 20 or less carbon atoms, or an amide bond-containing hydrocarbon group having 1 or more and 20 or less carbon atoms; $R^{14}$ represents a hydrocarbon group having 1 or more and 20 or less carbon atoms or an amide bond-containing hydrocarbon group having 1 or more and 20 or less carbon atoms; L represents a divalent organic group; $Q^-$ is a counter ion of the quaternary ammonium ion; r1 represents a number of 2 or more; plural $R^{11}$'s and $R^{12}$'s may be the same as or different from each other; and the bonding order among the structural units within the bracket does not matter, and the bonding form may be a block form or a random form), and

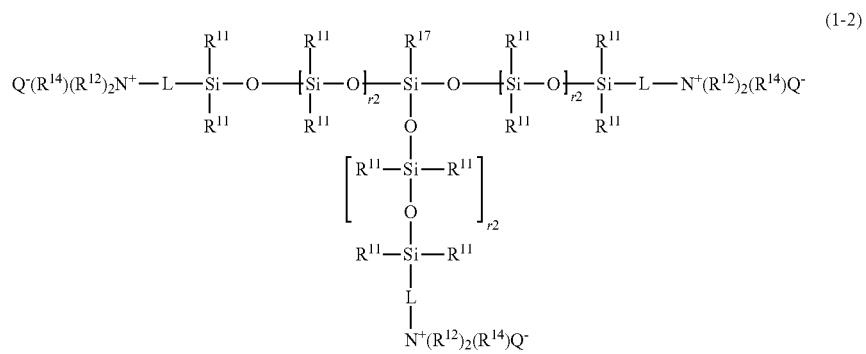

(1-2)

(in the formula (1-2), $R^{11}$, $R^{12}$, $R^{14}$, L, and $Q^-$ are the same as mentioned above; $R^{17}$ represents an alkyl group having 1 or more and 6 or less carbon atoms or a phenyl group; and r2 represents a number of 2 or more; and the bonding order among the structural units within the bracket does not matter, and the bonding form may be a block form or a random form), and (C) at least one cationic polymer selected from the group consisting of cationized guar gum, a cationized hydroxyalkyl cellulose, and a quaternized dialkylaminoalkyl (meth)acrylic acid salt polymer, wherein,
a mass ratio [(A)/(B)] of the component (A) to the component (B) is 50 to 1,000,
a mass ratio [(B)/(C)] of the component (B) to the component (C) is 0.03 to 0.4,
the content of the component (A) is 5 to 18% by mass,
the content of the component (B) is 0.01 to 0.2% by mass, and
the content of the component (C) is 0.3 to 1% by mass.

<7>
A detergent containing:
(A) at least one anionic surfactant selected from the group consisting of an alkyl sulfuric acid salt, an alkyl ether sulfuric acid salt, and an alkyl ether carboxylic acid salt,
(B) at least one selected from the group consisting of a quaternary ammonium cation-modified silicone represented by the following general formula (1-1) and a quaternary ammonium cation-modified silicone represented by the following general formula (1-2):

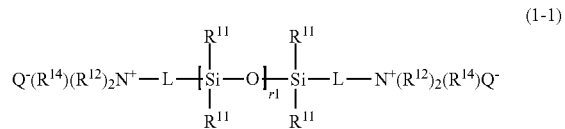

(in the formula (1-1), $R^{11}$ represents a hydrocarbon group having 1 or more and 6 or less carbon atoms; $R^{12}$ represents a hydrogen atom, a hydrocarbon group having 1 or more and 20 or less carbon atoms, or an amide bond-containing hydrocarbon group having 1 or more and 20 or less carbon atoms; $R^{14}$ represents a hydrocarbon group having 1 or more and 20 or less carbon atoms or an amide bond-containing hydrocarbon group having 1 or more and 20 or less carbon atoms; L represents a divalent organic group; Q is a counter ion of the quaternary ammonium ion; r1 represents a number of 2 or more; plural $R^{11}$'s and $R^{12}$'s may be the same as or different from each other; and the bonding order among the structural units within the bracket does not matter, and the bonding form may be a block form or a random form), and

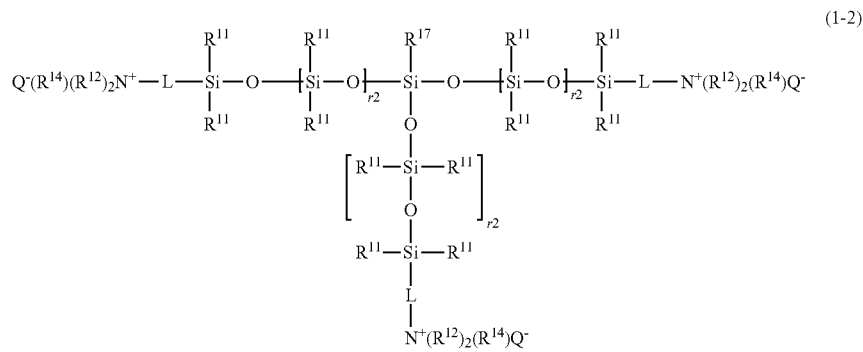

(in the formula (1-2), $R^{11}$, $R^{12}$, $R^{14}$, L, and Q are the same as mentioned above; $R^{17}$ represents an alkyl group having 1 or more and 6 or less carbon atoms or a phenyl group; and r2 represents a number of 2 or more; and the bonding order among the structural units within the bracket does not matter, and the bonding form may be a block form or a random form), and (C) at least one cationic polymer selected from the group consisting of cationized guar gum, a cationized hydroxyalkyl cellulose, and a quaternized dialkylaminoalkyl (meth)acrylic acid salt polymer, wherein, a mass ratio [(A)/(B)] of the component (A) to the component (B) is 50 to 1,000, a mass ratio [(B)/(C)] of the component (B) to the component (C) is 0.03 to 0.4, a mass ratio [(A)/(C)] of the component (A) to the component (C) is 10 to 40, the content of the component (A) is 5 to 18% by mass, the content of the component (B) is 0.01 to 0.2% by mass, and the content of the component (C) is 0.3 to 1% by mass.

<8>

The detergent as set forth in any one of <1> to <7>, which is a hair detergent.

<9>

A method for preventing entanglement of hair or fibers, the method including a step of washing hair or fibers by using the detergent as set forth in any one of <1> to <7>.

<10>

Use of the detergent as set forth in any one of <1> to <7> to hair or fibers.

EXAMPLES

The present invention is hereunder described by reference to Examples, but it should be construed that the present invention is not limited to the scope of the Examples. In the present Examples, various measurements and evaluations were performed by the following methods.

(pH Measurement)

The pH at 25° C. was measured using a pH meter (F-51, manufactured by Horiba, Ltd.). For the pH measurement of a hair detergent, an aqueous dispersion having a hair detergent diluted with purified water to 5% was used.

(Lathering Evaluation)

A hair bundle of untreated hairs of a Chinese person having a mass of 20 g and a length of 20 cm was damaged through a bleach treatment by a later-mentioned method with the following hair bleach and washed with the following plain shampoo, to obtain a hair bundle for lathering evaluation. This hair bundle for evaluation was thoroughly damped with warm water at 35 to 40° C. and then coated with 1 g of a hair detergent of each of the Examples, followed by washing for 1 minute.

The lathering evaluation was performed by five panelists, and by scoring the lowest as "1" and the highest as "5", respectively, a 5-grade evaluation was performed while defining Example 5 as a standard score 3. An average grade (rounded off to the first decimal place) of the evaluation by the five panelists was tabulated. The case where the average grade by the five panelists is score 3 or above is considered as passing, and when the average grade is score 4 or more, it may be said that an explicitly excellent performance is revealed.

(Evaluation Criteria)
5: Lathering is very good.
4: Lathering is good.
3: Lathering is moderate.
2: Lathering is bad.
1: Lathering is very bad.

[Composition of Plain Shampoo]

| Component | (% by mass) |
| --- | --- |
| Polyoxyethylene lauryl ether sulfuric acid Na | 11.3 (*1) |
| Coconut oil fatty acid N-methylethanolamide (*2) | 3.0 |
| Citric acid | 0.2 |
| Methyl paraben | 0.3 |
| Purified water | Balance |
| Total | 100.0 |

(*1): 42.0% by mass as EMAL E-27C (manufactured by Kao Corporation, active ingredient: 27% by mass)
(*2): AMINON C-11S (manufactured by Kao Corporation)

[Composition of Hair Bleach]

| Component | (% by mass) |
| --- | --- |
| Monoethanolamine | 1.5 |
| 28% by mass ammonia water | 4.0 |
| Ammonium bicarbonate | 1.0 |
| 35% by mass hydrogen peroxide water | 8.2 |
| Purified water | Balance |
| Total | 100.0 |

[Bleach Treatment Method]

A hair bundle of untreated hairs of a Chinese person having a mass of 20 g was coated with 20 g of the hair bleach, allowed to stand for 30 minutes, and then thoroughly rinsed with warm water at 35 to 40° C. This operation was repeated four times, thereby preparing a bleach-treated hair bundle.

(Measurement of Combing Load)

The aforementioned hair bundle for lathering evaluation was prepared, thoroughly damped with warm water at 35 to 40° C., and then coated with 1 g of a hair detergent of each of the Examples. The resulting hair bundle was lightly put between palms of both hands and washed for 1 minute while moving the hands so as to rub together. Thereafter, the hair bundle was rinsed with warm water for 30 seconds without allowing the fingers to pass therethrough, thereby obtaining a hair bundle for measurement of combing load.

The aforementioned hair bundle was set on a combing force measuring apparatus (manufactured by Utsunomiya-seiki Co., Ltd., "KOT-0303"), a comb (one in which ten pins having a diameter of 2 mm were linearly arranged at intervals of 4 mm) was allowed to pass through the uppermost part of the hair bundle, and a load (gf) applied when passing the comb through the hair ends was measured. The load was calculated at 200 points of the hair bundle having a length of 20 cm, and a total value of the 200 points in total was designated as "combing load". The smaller the value of combing load, the more excellent the effect for preventing entanglement, and when the combing load is 35,000 gf or less, the effect for preventing entanglement is especially excellent.

(Easiness of Brushing after Towel Drying)

The aforementioned hair bundle for lathering evaluation was prepared, thoroughly damped with warm water at 35 to 40° C., and then coated with 1 g of a hair detergent of each of the Examples. The resulting hair bundle was lightly put between palms of both hands without allowing the fingers to pass through the hair bundle and washed for 1 minute while moving the hands so as to rub together. Thereafter, the hair bundle was rinsed with warm water for 30 seconds without allowing the fingers to pass therethrough. The obtained hair bundle was placed on a towel, and the both surfaces of the hair bundle were covered by the towel and subjected to towel drying so as to rub together, thereby obtaining a hair bundle for brushing evaluation.

The aforementioned hair bundle was set on a combing force measuring apparatus (manufactured by Utsunomiya-seiki Co., Ltd., "KOT-0303"), the root of the hair bundle was put from both sides between two brushes, and an action of simultaneously stroking the brushes towards the hair end was repeated 10 times. A maximum load during one stroke was measured, and the number of strokes required until the load became not more than 400 gf was evaluated. It is meant that as the number of strokes shown in the table is small, after towel drying, the entanglement of hair is small, too, and the brushing is readily performed. The case where the maximum load was not more than 400 gf at stroke during one stroke is taken as "number of strokes: 0".

(Evaluation of Quick Drying Properties)

The aforementioned hair bundle for brushing evaluation was prepared, dried by blowing hot air with a hair dryer (manufactured by Can Co., Ltd., "Sobis TYPE 315", air volume setting: High) at a distance of 5 to 15 cm from the hair bundle while combing fingers, and a time until the wet hair returned to the weight in a dry state was measured (number of measurements: one time). It is meant that as the drying time is short, the quick drying properties are high.

Examples 1 to 15 and Comparative Examples 1 to 3 (Preparation and Evaluation of Hair Detergent)

A hair detergent of each of the Examples was prepared in the following way according to the blending shown in each table and evaluated.

First of all, the component (C) was dissolved or uniformly dispersed in water, an appropriate amount of water and other component than the component (B) and the component (B') were added, and the contents were heated to 80° C. and uniformly mixed, followed by cooling to 40° C. The component (B) and/or the component (B') were/was added thereto and uniformly mixed, and finally, the water which had been vaporized due to heating was replenished. Using this hair detergent, the lathering evaluation and the measurement of combing load were carried out by the aforementioned methods.

Examples 6 to 7, 9, and 13 to 15 and Comparative Examples 1 to 3 were evaluated for the easiness of brushing after towel drying and the quick drying properties by the aforementioned methods. In addition, Examples 8 and 10 to 12 were evaluated for the easiness of brushing after towel drying by the aforementioned method. The results are shown in Tables 1 to 4. The blending amounts shown in the tables are the active ingredient amount (% by mass) of each of the components.

TABLE 1

| | | | | Example | | | | | Comparative Example |
|---|---|---|---|---|---|---|---|---|---|
| | | | | 1 | 2 | 3 | 4 | 5 | 1 |
| Blending (% by mass) | (A) | Ammonium laureth sulfate | *1 | 10.0 | 10.0 | 10.0 | 10.0 | 10.0 | 10.0 |
| | (B) | Cation-modified silicone 1 (Quaternium-80) | *2 | 0.01 | 0.05 | 0.1 | | | 0.45 |
| | | Cation-modified silicone 2 (Silicone Quaternium-22) | *3 | | | | 0.1 | | |
| | | Cation-modified silicone 3 (Silicone Quaternium-22) | *4 | | | | | 0.1 | |
| | (C) | Polyquaternium-10 | *5 | 0.30 | 0.30 | 0.30 | 0.30 | 0.30 | 0.30 |
| | Others | pH modifier | | Amount at which the pH of the 5% aqueous dispersion becomes 5 | | | | | |
| | | Purified water | | Balance | | | | | |
| | | Mass ratio (A)/(B) | | 1000 | 200 | 100 | 100 | 100 | 22.2 |
| | | Mass ratio (B)/(C) | | 0.03 | 0.17 | 0.33 | 0.33 | 0.33 | 1.50 |
| | | Mass ratio (A)/(C) | | 33 | 33 | 33 | 33 | 33 | 33 |
| Evaluation | | Lathering | | 5 | 5 | 5 | 4 | 3 | 2 |
| | | Combing load (gf) | | 22452 | 48441 | 36939 | 37490 | 41687 | 70829 |
| | | Easiness of brushing after towel drying (Number of strokes required until the maximum load during one stroke became not more than 400 gf) | | — | — | — | — | — | 4 |
| | | Quick drying properties ((drying time)/sec) | | — | — | — | — | — | 138 |

*1: Manufactured by Kao Corporation, EMAL 170S-A (active ingredient: 70%)

*2: Manufactured by Evonik Industries AG, ABIL QUAT 3272 (active ingredient: 50%)

*3: Manufactured by Evonik Industries AG, ABIL TQUAT 60 (active ingredient: 60%)

*4: Manufactured by Evonik Industries AG, ABIL ME 45 (active ingredient: 30%)

*5: Manufactured by Kao Corporation, POIZ C-150L

TABLE 2

| | | | | Example | | | | Comparative Example |
|---|---|---|---|---|---|---|---|---|
| | | | | 6 | 7 | 8 | 9 | 2 |
| Blending (% by mass) | (A) | Ammonium laureth sulfate | *1 | 8.0 | 8.0 | 8.0 | 8.0 | 8.0 |
| | (B) | Cation-modified silicone 1 (Quaternium-80) | *2 | 0.130 | 0.115 | 0.100 | 0.090 | 0.400 |
| | (C) | Polyquaternium-10 | *3 | 0.40 | 0.40 | 0.40 | 0.40 | 0.40 |
| | Others | pH modifier | | Amount at which the pH of the 5% aqueous dispersion becomes 5 | | | | |
| | | Purified water | | Balance | | | | |
| | | Mass ratio (A)/(B) | | 61.5 | 69.6 | 80.0 | 88.9 | 20.0 |
| | | Mass ratio (B)/(C) | | 0.33 | 0.29 | 0.25 | 0.23 | 1.00 |
| | | Mass ratio (A)/(C) | | 20 | 20 | 20 | 20 | 20 |
| Evaluation | | Lathering | | 4 | 4 | 4 | 4 | 3 |
| | | Combing load (gf) | | 36942 | 28331 | 35104 | 45868 | 52416 |
| | | Easiness of brushing after towel drying (Number of strokes required until the maximum load during one stroke became not more than 400 gf) | | 0 | 1 | 1 | 1 | 4 |
| | | Quick drying properties ((drying time)/sec) | | 104 | 97 | — | 114 | 160 |

*1: Manufactured by Kao Corporation, EMAL 170S-A (active ingredient: 70%)
*2: Manufactured by Evonik Industries AG, ABIL QUAT 3272 (active ingredient: 50%)
*3: Manufactured by Kao Corporation, POIZ C-150L

TABLE 3

| | | | | Example | | | Comparative Example |
|---|---|---|---|---|---|---|---|
| | | | | 10 | 11 | 12 | 3 |
| Blending (% by mass) | (A) | Ammonium laureth sulfate | *1 | 8.0 | 8.0 | 8.0 | 8.0 |
| | (B) | Cation-modified silicone 1 (Quaternium-80) | *2 | 0.1 | 0.1 | 0.1 | 0.1 |
| | (C) | Polyquaternium-10 | *3 | 0.40 | 0.30 | 0.20 | 0.10 |
| | Others | pH modifier | | Amount at which the pH of the 5% aqueous dispersion becomes 5 | | | |
| | | Purified water | | Balance | | | |
| | | Mass ratio (A)/(B) | | 80.0 | 80.0 | 80.0 | 80.0 |
| | | Mass ratio (B)/(C) | | 0.25 | 0.33 | 0.50 | 1.00 |
| | | Mass ratio (A)/(C) | | 20 | 27 | 40 | 80 |
| Evaluation | | Lathering | | 4 | 5 | 4 | 2 |
| | | Combing load (gf) | | 35104 | 29790 | 50371 | 164838 |
| | | Easiness of brushing after towel drying (Number of strokes required until the maximum load during one stroke became not more than 400 gf) | | 1 | 1 | 2 | 5 |
| | | Quick drying properties ((drying time)/sec) | | — | — | — | 163 |

*1: Manufactured by Kao Corporation, EMAL 170S-A (active ingredient: 70%)
*2: Manufactured by Evonik Industries AG, ABIL QUAT 3272 (active ingredient: 50%)
*3: Manufactured by Kao Corporation, POIZ C-150L

TABLE 4

| | | | | Example | | |
|---|---|---|---|---|---|---|
| | | | | 13 | 14 | 15 |
| Blending (% by mass) | (A) | Ammonium laureth sulfate | *1 | 11 | 9 | 15 |
| | | Sodium laureth carboxylate | *2 | 0.7 | 1.2 | 0.1 |
| | (B) | Cation-modified silicone 1 (Quaternium-80) | *3 | 0.05 | 0.1 | |
| | | Cation-modified silicone 2 (Silicone Quaternium-22) | *4 | 0.05 | 0.1 | 0.1 |

TABLE 4-continued

|   |   |   |   | Example 13 | Example 14 | Example 15 |
|---|---|---|---|---|---|---|
|   | (C) | Polyquaternium-10 | *5 | 0.1 | 0.2 | 0.4 |
|   |   | Guar hydroxypropyltrimonium chloride | *6 | 0.5 | 0.3 | 0.1 |
|   |   | Polyquaternium-52 | *7 | 0.01 | 0.1 | 0.2 |
|   |   | PPG-2 hydroxypropyltrimonium cellulose | *8 | 0.2 | 0.01 | 0.1 |
|   | (D) | Lauramidopropyl betaine | *9 | 0.6 | 0.2 | 1.2 |
|   |   | Lauryl hydroxysultaine | *10 | 0.8 | 1.2 | 0.2 |
|   | (E) | Isodecyl glyceryl ether | *11 | 0.2 | 0.5 | 0.8 |
|   |   | PPG-3 caprylyl ether | *12 | 0.8 | 0.5 | 0.2 |
|   | (B') | Dimethicone | *13 | 0.20 | 0.70 | 1.2 |
|   | Others | Ethylene glycol distearate | *14 | 1.2 | 1.2 | 1.2 |
|   |   | Antiseptic |   | Moderate amount | | |
|   |   | pH modifier |   | Amount at which the pH of the 5% aqueous dispersion becomes 5 | | |
|   |   | Purified water |   | Balance | | |
|   |   | Mass ratio (A)/(B) |   | 117 | 51 | 151 |
|   |   | Mass ratio (B)/(C) |   | 0.12 | 0.33 | 0.13 |
|   |   | Mass ratio (A)/(C) |   | 14 | 17 | 19 |
|   |   | Mass ratio (A)/(D) |   | 8 | 7 | 11 |
|   |   | Mass ratio (A)/(E) |   | 12 | 10 | 15 |
|   |   | Mass ratio (A)/(B') |   | 59 | 15 | 13 |
| Evaluation |   | Lathering |   | 5 | 5 | 5 |
|   |   | Combing load (gf) |   | 35136 | 27024 | 23607 |
|   |   | Easiness of brushing after towel drying (Number of strokes required until the maximum load during one stroke became not more than 400 gf) |   | 1 | 1 | 1 |
|   |   | Quick drying properties ((drying time)/sec) |   | 89 | 79 | 82 |

*1: Manufactured by Kao Corporation, EMAL 170S-A (active ingredient: 70%)
*2: Manufactured by Kao Corporation, AKYPO LM-26SD (active ingredient: 19%)
*3: Manufactured by Evonik Industries AG, ABIL QUAT 3272 (active ingredient: 50%)
*4: Manufactured by Evonik Industries AG, ABIL ME 45 (active ingredient: 30%)
*5: Manufactured by Kao Corporation, POIZ C-150L
*6: Manufactured by Solvay S.A., JAGUAR C-14-S
*7: Manufactured by Kao Corporation, SOFCARE KG-101W-E (active ingredient: 2.4%)
*8: Manufactured by Kao Corporation, SOFCARE C-HP2W
*9: Manufactured by Kao Corporation, AMPHITOL 20AB
*10: Manufactured by Kao Corporation, AMPHITOL 20HD
*11: Manufactured by Kao Corporation, PENETOL GE-ID
*12: Manufactured by Kao Corporation, KAO SOFCARE GP-1
*13: Manufactured by Dow Toray Co., Ltd., DOWSIL BY22-029 (active ingredient: 50%)
*14: Manufactured by Kao Corporation, EMANON 3201M-V

INDUSTRIAL APPLICABILITY

In accordance with the detergent of the present invention, lathering during washing is favorable, and the generation of entanglement of a washing object, such as hair and fibers, even during washing and after washing can be substantially inhibited and solved without performing an operation of putting fingers through hair or the like. For example, in the case where the detergent of the present invention is a hair detergent, the entanglement in hair after washing and towel drying is hardly generated, and therefore, the hair can be dried for a short time, and finish after drying becomes favorable.

The invention claimed is:

1. A detergent, comprising:

(A) an anionic surfactant, (B) at least one selected from the group consisting of a quaternary ammonium cation-modified silicone represented by the following general formula (1-1) and a quaternary ammonium cation-modified silicone represented by the following general formula (1-2):

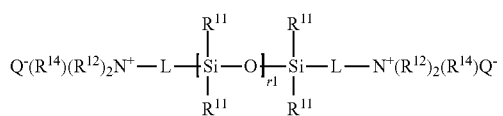

(1-1)

wherein: $R^{11}$ represents a hydrocarbon group having 1 or more and 6 or less carbon atoms;

$R^{12}$ represents a hydrogen atom, a hydrocarbon group having 1 or more and 20 or less carbon atoms, or an amide bond-containing hydrocarbon group having 1 or more and 20 or less carbon atoms;

$R^{14}$ represents a hydrocarbon group having 1 or more and 20 or less carbon atoms or an amide bond-containing hydrocarbon group having 1 or more and 20 or less carbon atoms;

L represents a divalent organic group;

$Q^-$ is a counter ion of the quaternary ammonium ion;

r1 represents a number of 2 or more;

plural $R^{11}$'s and $R^{12}$'s may be the same as or different from each other;

the bonding order among the structural units within the bracket does not matter;

the bonding form may be a block form or a random form, and

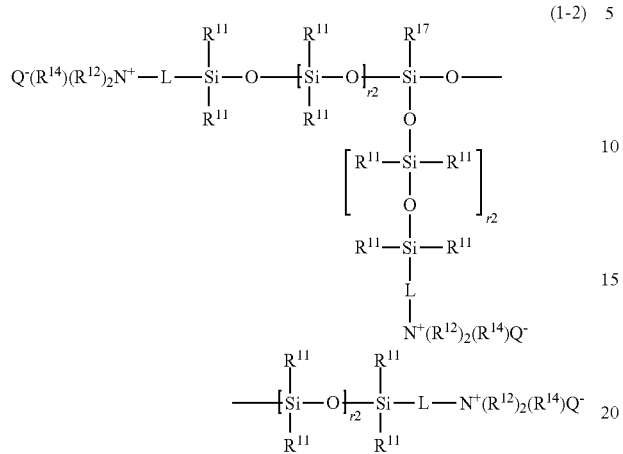

(1-2)

wherein:
$R^{11}$, $R^{12}$, $R^{14}$, L, and Q are the same as mentioned above;
$R^{17}$ represents an alkyl group having 1 or more and 6 or less carbon atoms or a phenyl group;
r2 represents a number of 2 or more;
the bonding order among the structural units within the bracket does not matter; and
the bonding form may be a block form or a random form, and (C) a cationic polymer,
wherein a mass ratio [(A)/(B)] of the component (A) to the component (B) is 30 or more and 5,000 or less, and a mass ratio [(B)/(C)] of the component (B) to the component (C) is 0.01 or more and 0.33 or less,
wherein the component (A) is one or more members selected from the group consisting of an alkyl ether sulfate and an alkyl ether carboxylate,
wherein the component (C) is one or more members selected from the group consisting of a cationized polygalactomannan, a cationized hydroxyalkyl cellulose, a quaternized dialkylaminoalkyl (meth)acrylic acid salt polymer, and a diallyl quaternary ammonium salt polymer, and
wherein the detergent provides a combing load of 45.868 gf or less.

2. The detergent according to claim 1, further comprising, as a component (D), an ampholytic surfactant.

3. The detergent according to claim 1, further comprising, as a component (E), a nonionic surfactant.

4. The detergent according to claim 1, further comprising, as a component (B'), a silicone other than the component (B).

5. The detergent according to claim 1, wherein the content of the component (A) is 1% by mass or more and 30% by mass or less.

6. The detergent according to claim 1, wherein the content of the component (B) is 0.001% by mass or more and 3% by mass or less.

7. The detergent according to claim 1, which is a hair detergent.

8. The detergent according to claim 1, wherein the mass ratio [(A)/(B)] of the component (A) to the component (B) is 50 to 500.

9. A method for preventing entanglement of hair or fibers, the method comprising washing hair or fibers with the detergent of claim 1.

* * * * *